US012202937B2

(12) United States Patent
Zhao

(10) Patent No.: US 12,202,937 B2
(45) Date of Patent: Jan. 21, 2025

(54) CYCLIC AMIDE INITIALIZED POLYETHERAMINE AND USES THEREOF

(71) Applicant: Huntsman Petrochemical LLC, The Woodlands, TX (US)

(72) Inventor: Haibo Zhao, The Woodlands, TX (US)

(73) Assignee: HUNTSMAN PETROCHEMICAL LLC

( * ) Notice: Subject to any disclaimer, the term of this patent is extended or adjusted under 35 U.S.C. 154(b) by 714 days.

(21) Appl. No.: 17/279,220

(22) PCT Filed: Jul. 29, 2019

(86) PCT No.: PCT/US2019/043871
§ 371 (c)(1),
(2) Date: Mar. 24, 2021

(87) PCT Pub. No.: WO2020/068262
PCT Pub. Date: Apr. 2, 2020

(65) Prior Publication Data
US 2022/0033579 A1 Feb. 3, 2022

Related U.S. Application Data

(60) Provisional application No. 62/736,124, filed on Sep. 25, 2018.

(51) Int. Cl.
*C08G 65/26* (2006.01)
*C09D 11/326* (2014.01)
*C10L 1/2387* (2006.01)

(52) U.S. Cl.
CPC ........ *C08G 65/2633* (2013.01); *C09D 11/326* (2013.01); *C10L 1/2387* (2013.01); *C08G 2650/50* (2013.01)

(58) Field of Classification Search
CPC ............ C08G 65/2633; C08G 2650/50; C08G 73/024; C09D 11/326; C10L 1/2387
See application file for complete search history.

(56) References Cited

U.S. PATENT DOCUMENTS

| 3,152,998 | A | 10/1964 | Moss |
| 3,347,926 | A | 10/1967 | Zech |
| 3,654,370 | A | 4/1972 | Yeakey |
| 4,014,933 | A | 3/1977 | Boettger et al. |
| 4,152,353 | A | 5/1979 | Habermann |
| 4,304,690 | A | 12/1981 | Schulze et al. |
| 4,766,245 | A | 8/1988 | Larkin et al. |
| 5,507,843 | A | 4/1996 | Lin et al. |
| 5,837,867 | A * | 11/1998 | Lin .......................... C10L 1/232 44/337 |
| 5,912,189 | A | 6/1999 | Wolak et al. |
| 6,261,327 | B1 | 7/2001 | Graham et al. |
| 2007/0100024 | A1 | 5/2007 | Gu et al. |

FOREIGN PATENT DOCUMENTS

| WO | 2015028193 A1 | 3/2015 |
| WO | 2015073575 A2 | 5/2015 |
| WO | 2015144497 A1 | 10/2015 |

OTHER PUBLICATIONS

Corresponding Application in India Patent Application No. 202147012741; First Examination Report (FER) issued Sep. 16, 2023 and Hearing Notice issued Nov. 17, 2023.
PubChem-CID-123949728, Create Date: Jan. 25, 2017, p. 2 Fig.
PubChemCID-67748669, Creat Date: Nov. 30, 2012, p. 2, Fig.
International Search Report and Written Opinion received in corresponding PCT Application PCT/US2019/043871, completed Sep. 19, 2019 and mailed Oct. 16, 2019.

* cited by examiner

*Primary Examiner* — Shane Fang
(74) *Attorney, Agent, or Firm* — HUNTSMAN PETROCHEMICAL; Aleece Hayes

(57) ABSTRACT

A polyetheramine produced from a cyclic amide initiator which is first alkoxylated and then reductively aminated to form the polyetheramine. The polyetheramine of the present disclosure may be used in a variety of applications, such as a raw material in the synthesis of a dispersant for use in an aqueous pigment dispersion or as a fuel additive in a hydrocarbon fuel composition.

16 Claims, No Drawings

CYCLIC AMIDE INITIALIZED POLYETHERAMINE AND USES THEREOF

CROSS REFERENCE TO RELATED APPLICATIONS

The present application is the National Phase of International Application PCT/US2019/043871 filed Jul. 29, 2019 which designated the U.S. and which claims priority to U.S. Provisional Patent Application Ser. No. 62/736,124, filed Sep. 25, 2018, the entire contents of which is hereby expressly incorporated herein by reference.

STATEMENT REGARDING FEDERALLY SPONSORED RESEARCH OR DEVELOPMENT

Not applicable.

FIELD

The present disclosure is generally directed to a cyclic amide initialized polyetheramine and its use in various applications, including, but not limited to, as a dispersant for pigments and as an additive in fuel compositions.

BACKGROUND

Polyetheramines are compounds containing at least one polyalkylene glycol group and at least one amine group. The manufacture of these materials is well known and generally includes the reaction of an alcohol or alkyl phenol initiator with an alkylene oxide to form an intermediate polyol, which in turn, is reductively aminated to form the polyetheramine. More specific processes can be found in, for example:

U.S. Pat. No. 3,347,926 which discloses polyetheramines produced from the alkoxylation of aliphatic monohydric alcohols and their subsequent conversion into polyetheramines with ammonia and hydrogen in the presence of a catalyst;

U.S. Pat. No. 3,654,370 which describes polyetheramines prepared by the addition of ethylene oxide, propylene oxide or mixtures thereof to ethylene glycol, propylene glycol, glycerin or trimethylolpropane to form intermediates and their subsequent treatment with ammonia and hydrogen over a catalyst;

U.S. Pat. No. 4,304,690 which discloses polyetheramines prepared by the addition of an alkylene oxide to an alky phenol to form an alkoxylated intermediate and replacement of the hydroxyl group by a primary amino group during the subsequent reaction with ammonia and hydrogen in the presence of a catalyst;

U.S. Pat. No. 4,766,245 which describes a process of making polyetheramines by the reductive amination of hydroxyl-terminated polyoxyalkylene compounds in the presence of a Raney nickel/aluminum catalyst; and more recently, WO 2015/028193 and WO 2015/144497 which disclose polyetheramines produced from glycerol, trimethylolpropane and 1,2-dialcohol initiators.

In spite of the above, there is a continued need to develop new, versatile, polyetheramines produced from non-alcohol or non-alkyl phenol initiators which can replace state of the art polyetheramines and provide similar or improved performance during use in various applications.

SUMMARY

The present disclosure describes a polyetheramine comprising a compound having a formula (I)

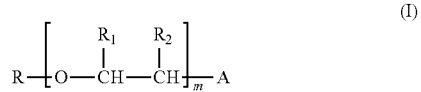

where R is a cyclic amide group having the formula (II)

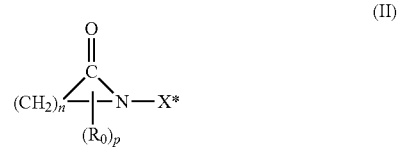

where n is an integer of from 3 to 15, $R_0$ is a substituent that can replace hydrogen in any hydrocarbon portion of the cyclic amide group and is an alkyl group or an aryl group, p is an integer of from 0 to 2n, and X* denotes the attachment site of the cyclic amide group to the rest of the polyetheramine compound; $R_1$ and $R_2$ are each independently hydrogen, methyl or ethyl and each $R_1$ and $R_2$ is independently selected in each $—O—CHR_1—CHR_2—$ unit; A is $NH_2$ or an N-alkyl amino having 1 to about 20 carbon atoms in the alkyl group; and, m is an integer ranging from about 2 to about 200.

DETAILED DESCRIPTION

The present disclosure provides a cyclic amide initialized polyetheramine and its use in various applications. It has been surprisingly found the cyclic amide initialized polyetheramine of the present disclosure may provide at least equal to, or in some embodiments, improved performance as compared to state of the art polyetheramines. Without being bound by theory, it is believed that the amide group in the initiator can allow the subsequently produced polyetheramine to exhibit more hydrophilicity (i.e. the amide group may form strong hydrogen bonds with protic solvents, such as water) than state of the art polyetheramines. Thus, the inventive polyetheramines are expected to exhibit at least equal, if not improved, dispersing capabilities as compared to those for state of the art polyetheramines.

If appearing herein, the term "comprising" and derivatives thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The terms "or" and "and/or", unless stated otherwise, refer to the listed members individually as well as in any combination. For example, the expression A and/or B refers to A alone, B alone, or to both A and B.

The articles "a" and "an" are used herein to refer to one or to more than one (i.e. to at least one) of the grammatical objects of the article. By way of example, "an amine" means one amine or more than one amine. The phrases "in one embodiment", "according to one embodiment" and the like generally mean the particular feature, structure, or characteristic following the phrase is included in at least one embodiment of the present disclosure, and may be included in more than one embodiment of the present disclosure. Importantly, such phrases do not necessarily refer to the same embodiment. If the specification states a component or feature "may", "can", "could", or "might" be included or have a characteristic, that particular component or feature is not required to be included or have the characteristic.

The terms "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the present disclosure.

The term "alkyl" refers to a monovalent radical of an alkane. Suitable alkyl groups can have up to about 20 carbon atoms, or up to 16 carbon atoms, or up to 12 carbon atoms, or up to 10 carbon atoms, or up to 8 carbon atoms, or up to 6 carbon atoms, or up to 4 carbon atoms, or up to 3 carbon atoms. The alkyl groups may be linear, branched, cyclic, or a combination thereof.

The term "aryl" refers to a carbocyclic aromatic ring containing from 5 to 14 ring atoms. The ring atoms of a carbocyclic aryl group are all carbon atoms. The aryl ring structures include compounds having one or more ring structure such as mono-, bi-, or tricyclic compounds as well as benzo-fused carbocyclic moieties such as 5,6,7,8-tetrahydronaphthyl and the like. Specifically, the aryl group may be a mono-, bi-, or tricyclic ring. Representative aryl groups include phenyl, anthracenyl, fluorenyl, indenyl, azulenyl, phenanthrenyl and naphthyl.

The term "arylalkyl" refers to an alkyl group in which one or more hydrogen atoms in the alkyl group is replaced by an aryl group.

The term "N-alkylamino" refers to the group —NHR$_a$, where R$_a$ is an alkyl group.

According to one embodiment, the present disclosure provides a cyclic amide initialized polyetheramine comprising a compound having a formula (I):

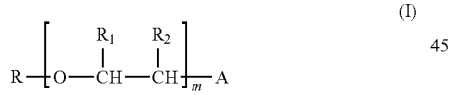

where R is a cyclic amide group having the formula (II)

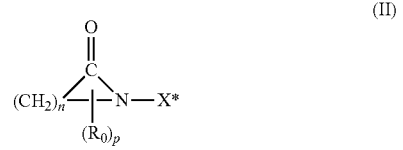

where n is an integer of from 3 to 15, R$_0$ is a substituent that can replace hydrogen in any hydrocarbon portion of the cyclic amide group and is an alkyl group or an aryl group, p is an integer of from 0 to 2n, and X* denotes the attachment site of the cyclic amide group to the rest of the cyclic amide initialized polyetheramine compound; R$_1$ and R$_2$ are each independently hydrogen, methyl or ethyl and each R$_1$ and R$_2$ is independently selected in each —O—CHR$_1$—CHR$_2$— unit;

A is NH$_2$ or an N-alkyl amino having 1 to about 20 carbon atoms in the alkyl group; and, m is an integer ranging from about 2 to about 200. Accordingly, the above polyetheramine of formula (II) may include, without limitation, homopolymers, and both random and block polymers and co-polymers of any one or more of the following, either alone or mixed with one another in any proportion: oxyethylene, oxypropylene, and oxybutylene units.

In one embodiment, R is a cyclic amide group having the formula (II) where n is an integer of from 3 to 12, R$_0$ is an alkyl group, p is an integer of from 0 to 4 and X* denotes the attachment site of the cyclic amide group to the rest of the cyclic amide initialized polyetheramine compound. In another embodiment R is a cyclic amide group having the formula (II) where n is an integer of from 3 to 8, R$_0$ is a C$_1$-C$_4$ alkyl group, p is an integer of from 0 to 2 and X* denotes the attachment site of the cyclic amide group to the rest of the cyclic amide initialized polyetheramine compound. In still another embodiment, R is a cyclic amide group having the formula (II) where n is an integer of from 3 to 7, p is 0 and X* denotes the attachment site of the cyclic amide group to the rest of the cyclic amide initialized polyetheramine compound. Examples of cyclic amide groups include, but are not limited to:

a compound having a formula

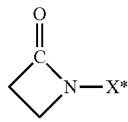

a compound having a formula

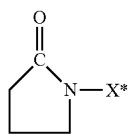

a compound having a formula

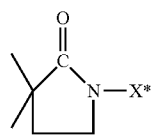

a compound having a formula

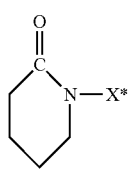

a compound having a formula

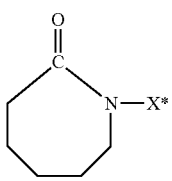

a compound having a formula

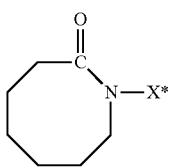

a compound having a formula

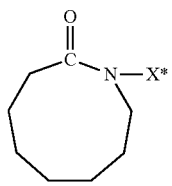

and a compound having a formula

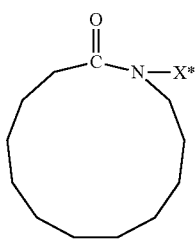

According to another embodiment, R is a cyclic amide group having the formula (II); $R_1$ and $R_2$ are each independently hydrogen, methyl or ethyl and each $R_1$ and $R_2$ is independently selected in each —O—$CHR_1$—$CHR_2$— unit with the proviso that at least one of $R_1$ or $R_2$ is hydrogen; A is $NH_2$; and, m is an integer ranging from about 2 to about 150 or from about 2 to about 100 or from about 2 to about 50 or even from about 2 to about 40.

In another embodiment, R is a cyclic amide group having the formula (II); $R_1$ and $R_2$ are each independently hydrogen or methyl and each $R_1$ and $R_2$ is independently selected in each —O—$CHR_1$—$CHR_2$— unit with the proviso that at least one of $R_1$ or $R_2$ is hydrogen; A is $NH_2$; and, m is an integer ranging from about 2 to about 150 or from about 2 to about 100 or from about 2 to about 50 or even from about 2 to about 40.

In still another embodiment, R is a cyclic amide group having the formula (II); $R_1$ and $R_2$ are each independently hydrogen or ethyl and each $R_1$ and $R_2$ is independently selected in each —O—$CHR_1$—$CHR_2$— unit with the proviso that at least one of $R_1$ or $R_2$ is hydrogen; A is $NH_2$; and, m is an integer ranging from about 2 to about 150 or from about 2 to about 100 or from about 2 to about 50 or even from about 2 to about 40.

The cyclic amide initialized polyetheramine compound of formula (I) can be prepared by methods known to those skilled in the art. For example, it can be prepared utilizing a cyclic amide having the formula (II) above where X* is hydrogen as an initiator that is first charged to an alkoxylation reaction zone.

After charging, the initiator is contacted with an alkylene oxide in the alkoxylation reaction zone for a period of time sufficient to provide an intermediate polyol. The alkylene oxide may be ethylene oxide, propylene oxide, butylene oxide or any mixture thereof. In other embodiments, the alkylene oxide may be ethylene oxide, propylene oxide or a mixture thereof. In still other embodiments, the alkylene oxide may be butylene oxide.

The amount of alkylene oxide which is contacted with the initiator may range from about 1.2 to about 1.8 moles, and in some instances from about 1.4 to about 1.6 moles, of alkylene oxide per mole of initiator. Additionally, the period of time the initiator is contacted with the alkylene oxide is a period of time sufficient to form the intermediate polyol and in some instances may range from about 0.5 hours to about 24 hours.

The alkoxylation reaction zone can be a closed reaction vessel with alkoxylation being carried out under elevated temperature and pressure and in the presence of a base catalyst. For example, alkoxylation may be conducted at a temperature ranging from about 50° C. to about 150° C. and at a pressure ranging from about 40 psi to about 100 psi. The base catalyst may be any alkaline compound customarily used for base-catalyzed reactions, for example, an alkali metal hydroxide such as sodium hydroxide, lithium hydroxide, potassium hydroxide, or cesium hydroxide, or a tertiary amine, such as dimethyl cyclohexylamine or 1,1,3,3-tetramethylguanidine. After alkoxylation, the resulting product may be vacuum stripped to remove any unnecessary components, such as excess unreacted alkylene oxide, water and/or base catalyst, while leaving the resulting intermediate polyol.

The intermediate polyol is then used as a feedstock in a reductive amination step. In some instances, prior to reductive amination, the intermediate polyol is neutralized with acid or a chemical adsorbent, such as for example, oxalic acid or magnesium silicate, and filtered for the removal of insoluble materials. The intermediate polyol is charged to a reductive amination zone where it is brought into contact with a reductive amination catalyst, sometimes referred to as a hydrogenation-dehydrogenation catalyst, and reductively aminated in the presence of hydrogen and ammonia or a primary alkyl amine under reductive amination conditions. Reductive amination conditions may include, for example, a temperature within the range of about 150° C. to about 275° C. and a pressure within the range of about 500 psi to about 5000 psi or with a temperature within the range of about 180° C. to about 220° C. and pressure within the range of about 100 psi to about 2500 psi being used in some embodiments.

In one embodiment, the primary alkyl amine contains 1 nitrogen atom and from about 1 to about 20 carbon atoms, or from about 1 to about 6 carbon atoms, or even from about 1 to about 4 carbon atoms. Examples of primary alkyl amines include, but are not limited to, N-methylamine, N-ethylamine, N-propylamine, N-isopropylamine, N-butylamine, N-isobutylamine, N-sec-butylamine, N-tert-butylamine, N-pentylamine, N-cyclopentylamine, N-hexylamine, N-cyclohexylamine, N-octylamine, N-decylamine, N-dodecylamine, N-octadecylamine, N-benzylamine, N-(2-phenylethyl)amine, 2-aminoethanol, 3-amino-1-propanol, 2-(2-aminoethoxy)ethanol, N-(2-methoxyethyl)amine and N-(2-ethoxyethyl)amine and the like.

Any suitable hydrogenation catalyst may be used, such as those described in U.S. Pat. No. 3,654,370, the contents of which are incorporated herein by reference. In some embodiments, the hydrogenation catalyst may comprise one or more of the metals of group VIIIB of the Periodic Table, such as iron, cobalt, nickel, ruthenium, rhodium, palladium, and platinum, mixed with one or more metals of group VIB of the Periodic Table such as chromium, molybdenum or tungsten. A promoter from group IB of the Periodic Table, such as copper, may also be included. As an example, a catalyst may be used comprising from about 60 mole percent to about 85 mole percent of nickel, about 14 mole percent to about 37 mole percent of copper and about 1 mole percent to about 5 mole percent of chromium (as chromia), such as a catalyst of the type disclosed in U.S. Pat. No. 3,152,998. As another example, a catalyst of the type disclosed in U.S. Pat. No. 4,014,933 may be used containing from about 70% by weight to about 95% by weight of a mixture of cobalt and nickel and from about 5% by weight to about 30% by weight of iron. As another example, a catalyst of the type disclosed in U.S. Pat. No. 4,152,353 may be used, comprising nickel, copper and a third component which may be iron, zinc, zirconium or a mixture thereof, for example, a catalyst containing from about 20% by weight to about 49% by weight of nickel, about 36% by weight to about 79% by weight of copper and about 1% by weight to about 15% by weight of iron, zinc, zirconium or a mixture thereof. As still another example, a catalyst of the type described in U.S. Pat. No. 4,766,245 may be used comprising about 60% by weight to about 75% by weight of nickel and about 25% by weight to about 40% by weight of aluminum.

The reductive amination may be conducted on a continuous basis with the intermediate polyol, ammonia or primary alkyl amine and hydrogen being continuously charged to a reactor containing a fixed bed of reductive amination catalyst and with product being continually withdrawn.

The product is suitably depressured so as to recover excess hydrogen and ammonia or primary alkyl amine for recycle and is then fractionated to remove by-product water of reaction to provide the inventive polyetheramine.

During reductive amination, the reductive amination conditions which may also be utilized include the use of from about 4 moles to about 150 moles of ammonia or primary amine per hydroxyl equivalent of intermediate polyol feedstock. Hydrogen may be used in an amount ranging from about 0.5 mole equivalents to about 10 mole equivalents of hydrogen per hydroxyl equivalent of intermediate polyol feedstock. The contact times within the reaction zone, when the reaction is conducted on a batch basis, may be within the range of from about 0.1 hours to about 6 hours or from about 0.15 hours to about 2 hours.

When the reaction is conducted on a continuous basis using catalyst pellets, reaction times may be from about 0.1 grams to about 2 grams of feedstock per hour per cubic centimeter of catalyst and, more preferably, from about 0.3 grams to about 1.6 grams of precursor feedstock per hour per cubic centimeter of catalyst. Also, the reductive amination may be conducted in the presence of about 1 mole to about 200 moles of ammonia or primary alkyl amine per mole of intermediate polyol or from about 4 moles to about 130 moles of ammonia or primary alkyl amine per mole of intermediate polyol. From about 0.1 moles to about 50 moles of hydrogen per mole of intermediate polyol may be employed or from about 1 mole to about 25 moles of hydrogen per mole of intermediate polyol.

The novel cyclic amide initialized polyetheramines of formula (I) are useful in a variety applications, including, but not limited to, as a wetting and dispersing agent for organic and inorganic pigments, dyestuffs, and color brighteners or as a fuel additive in a hydrocarbon fuel composition. Other applications may include their use as a cement additive and in oil & gas field applications, such as a corrosion inhibitor, a demulsifier and an acid retarding agent.

In one particular embodiment, the polyetheramine of formula (I) is a dispersant which is capable of facilitating the formation of a variety of pigments to provide stable pigment dispersions in which the pigment is provided substantially at the primary particle size of the pigment with the highest pigment loading possible at a desired viscosity. In another particular embodiment, the dispersant is a reaction product of the polyetheramine of formula (I) and a copolymer comprised of polymerized units of an alkenyl aromatic monomer and an $\alpha,\beta$-unsaturated carboxylic acid moiety.

The alkenyl aromatic monomer may be any compound containing an ethylenically unsaturated functional group attached directly to an aromatic radical. Such compounds correspond to the general formula

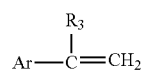

where Ar represents an aryl group such as phenyl or naphthyl and $R_3$ is hydrogen or methyl. The aryl group may be substituted with one or more substituents such as alkoxy, aryl, carboxy, hydroxy, nitro, cyano, halogen and alkyl. Illustrative alkenyl aromatic monomers which may be used for use in the copolymer include styrene, $\alpha$-methyl styrene, aromatic substituted (ortho-, meta-, or para-) methyl styrene, ethyl styrene, isopropyl styrene, tert-butyl styrene, chlorostyrene, bromostyrene, vinyl naphthalene, acetoxystyrene, methoxystyrene, hydroxystyrene, cyanostyrene, vinyl xylene, nitrostyrene, benzyl styrene and mixtures thereof. In one embodiment, the alkenyl aromatic monomer is styrene due to its low cost and high reactivity when copolymerized with $\alpha,\beta$-unsaturated carboxylic acid moieties.

The $\alpha,\beta$-unsaturated carboxylic acid moiety may be any ethylenically unsaturated organic compound which is copolymerizable with the alkenyl aromatic monomer and which contains a carboxylic functional group reactive with the amino group of the polyetheramine of formula (I). The carboxylic functional group may be an acid, ester, imide, or anhydride. The $\alpha,\beta$-unsaturated carboxylic acid moiety is therefore most suitably either as an $\alpha,\beta$-unsaturated dicarboxylic acid anhydride, $\alpha,\beta$-unsaturated dicarboxylic diacid, $\alpha,\beta$-unsaturated monocarboxylic acid, $\alpha,\beta$-unsaturated dicarboxylic acid ester (mono- or di-) and $\alpha,\beta$-unsaturated dicarboxylic acid imide. Different types of carboxylic acid moieties may be present.

In one embodiment, an $\alpha,\beta$-unsaturated dicarboxylic acid anhydride is preferred since the anhydride functionality may be readily reacted with the polyetheramine of formula (I) to form amide linkages. Comonomers of this type have the following general structure prior to copolymerization:

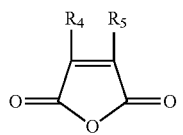

where $R_4$ and $R_5$ are the same or different and are independently selected from hydrogen, halogen, a $C_1$-$C_{10}$ alkyl group, an aryl group and an arylalkyl group. Examples of α,β-unsaturated dicarboxylic acid anhydrides include, but are not limited to, maleic anhydride, citraconic anhydride, ethyl maleic anhydride, methyl itaconic anhydride, dibromomaleic anhydride, itaconic anhydride, chloromaleic anhydrides, dichloromaleic anhydride, phenyl maleic anhydride, aconitic anhydride and mixtures thereof.

The α,β-unsaturated carboxylic acid moiety may alternatively be an α,β-unsaturated dicarboxylic diacid, diester, or half-acid, half-ester corresponding to the general structure:

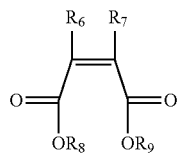

where $R_6$ and $R_7$ are the same or different and are independently selected from hydrogen, halogen, a $C_1$-$C_{10}$ alkyl group, an aryl group and an arylalkyl group, and $R_8$ and $R_9$ are the same or different and are independently selected from hydrogen, a $C_1$-$C_{10}$ alkyl group, an aryl group and an arylalkyl group. Examples of α,β-unsaturated dicarboxylic diacids include, but are not limited to, maleic acid, fumaric acid, itaconic acid, citraconic acid, mesaconic acid, ethyl maleic acid, methyl itaconic acid, chloromaleic acid, dichloromaleic acid, bromomaleic acid, dibromo maleic acid, phenylmaleic acid and mixtures thereof. Methyl, ethyl, propyl, butyl, benzyl, or phenyl mono- or diesters of these diacids may also be used.

In another embodiment, an α,β-unsaturated monocarboxylic acid or ester may be utilized which has the general structure:

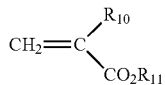

where $R_{10}$ and $R_{11}$ are the same or different and are independently selected from hydrogen, a $C_1$-$C_{10}$ alkyl group, an aryl group, and an arylalkyl group. Illustrative examples of comonomers of this type include but are not limited to, acrylic acid, methacrylic acid, methyl acrylate, methyl methacrylate, ethyl acrylate, ethyl methacrylate, butyl acrylate, 2-ethylhexyl acrylate and mixtures thereof.

The imide analogues of the α,β-unsaturated dicarboxylic acid anhydrides discussed hereinabove may also be employed as comonomers in the thermoplastic copolymer wherein the anhydride oxygen atom is replaced by $NR_{12}$. The $R_{12}$ group may be hydrogen, an alkyl group (for e.g., methyl, ethyl), an arylalkyl group (for e.g., benzyl, phenethyl) or an aryl group (for e.g., phenyl).

In one particular embodiment, the copolymer is comprised of polymerized units of styrene and maleic anhydride.

In another embodiment, the alkenyl aromatic monomer polymerized units comprise more than 50 mole percent of the copolymer with the α,β-unsaturated carboxylic acid moiety polymerized units comprising less than 50 mole percent of the copolymer. In yet another embodiment, the copolymer is comprised of from at least 50 weight percent, or at least 60 weight percent, or at least 70 weight percent, or at least 80 weight percent, or at least 90 weight percent alkenyl aromatic monomer polymerized units, based on the total weight of the copolymer, and less than 50 weight percent, or less than 40 weight percent, or less than 30 weight percent or less than 20 weight percent or less than 10 weight percent α,β-unsaturated carboxylic acid moiety polymerized units, based on the total weight of the copolymer. In a still further embodiment, the copolymer is comprised of from at least 70 weight percent to 97 weight percent alkenyl aromatic monomer polymerized units, based on the total weight of the copolymer, and from at least 3 weight percent to 30 weight percent α,β-unsaturated carboxylic acid moiety polymerized units, based on the total weight of the copolymer.

The polymerization may carried out by known batchwise or continuous polymerization methods, such as mass suspension, precipitation or solution polymerization and initiation with suitable free radical chain initiators, for example, hydroperoxides, peroxides or azo compounds, such as dilauroyl peroxide, dibenzoyl peroxide, tert-butyl perpivalate, tert-butyl permaleate, tert-butyl perbenzoate, dicumyl peroxide, tert-butyl cumyl peroxide, di-tert-butyl peroxide, cumyl hydroperoxide, tert-butyl hydroperoxide, 2.2'-azobis (Z-methylpropanenitrile), 2.2'-azobis(2-methylbutyronitrile) and mixtures thereof. In general, these initiators are used in amounts of from 0.1% to 20% by weight, or from 0.2% to 10% by weight, based on the total weight of the alkenyl aromatic monomer and α,β-unsaturated carboxylic acid moiety.

The polymerization may carried out as a rule at temperatures of about 40° C.-400° C. or about 80° C.-250° C., pressure expediently being used when α,β-unsaturated carboxylic acid moieties or solvents having boiling points below the polymerization temperature are used. The polymerization may be carried out in the absence of air, for example, under nitrogen, since oxygen interferes with the polymerization. In choosing the initiator or the initiator system, it is expedient to ensure that the half-life of the initiator or of the initiator system at the chosen polymerization temperature is less than 3 hours.

Apparatuses suitable for the polymerization are, for example, conventional stirred vessels having, for example, anchor stirrers, paddle stirrers, impeller stirrers or multistage impulse countercurrent agitators, and for the continuous preparation, stirred vessel cascades, tube reactors or static mixers.

In one embodiment, the preferred process for the preparation of the copolymers is solution polymerization. It is carried out in solvents in which the alkenyl aromatic monomer and α,β-unsaturated carboxylic acid moiety and the resulting copolymer are soluble. Suitable solvents for this purpose are all those which meet these requirements and which do not react with the alkenyl aromatic monomer and α,β-unsaturated carboxylic acid moiety and with the resulting copolymer. These are, for example, organic, preferably aromatic and/or aliphatic, solvents such as cumene, toluene, xylene, ethylbenzene, decane, pentadecane or commercial solvent mixtures.

In the preparation, the alkenyl aromatic monomer and α,β-unsaturated carboxylic acid moiety may be initially introduced and may be polymerized by adding a free radical chain initiator and with the supply of heat.

After polymerization, the copolymer that is obtained is reacted with the polyetheramine of formula (I). The preparation of the reaction product of the copolymer and polyetheramine of formula (I) may be carried out at temperatures of from about 50° C. to about 250° C., or from about 60° C. to about 200° C. While amides are formed at temperatures below 100° C., imides can be formed at higher temperatures. In some embodiments, the polyetheramine of formula (I) may be used in amounts of from about 0.001 mole to about 2 mole per mole of copolymer, or from about 0.01 mole to about 1 mole per mole of copolymer, or from about 0.5 mole to about 0.95 mole per mole of copolymer.

In one embodiment, the copolymer is initially introduced and the polyetheramine of formula (I) is then subsequently metered in. However, it is also possible for all starting materials to be mixed at room temperature and caused to react by increasing the temperature. In addition, the components may be allowed to react in solution using an organic solvent or mixture of solvents capable of dissolving the components. Such organic solvents include, but are not limited to, ethers such as tetrahydrofuran, aromatic hydrocarbons, such as toluene, and halogenated hydrocarbons, such as methylene chloride.

In one embodiment, when the α,β-unsaturated carboxylic acid moiety in the copolymer is an anhydride, the polyetheramine of formula (I) reacts to form a half-amide, half-acid which can possibly be converted to an imide by dehydration.

The reaction conditions will vary depending upon the reactivity of the individual components. For instance, when the copolymer contains anhydride groups, the reaction will generally take place rapidly at relatively low temperature since the anhydride ring is opened rather easily by the polyetheramine. If the copolymer contains acid, imide, or ester groups however, more vigorous reaction conditions may be necessary. The rate of reaction may be increased in such instances by the use of an appropriate catalyst, higher reaction temperatures or by removing any volatile coproducts which may be generated. Where the carboxylic group in the copolymer is a carboxylic acid, for example, it may be helpful to combine the components under vacuum in order to remove the water formed during reaction. Likewise, if the copolymer contains carboxylic ester groups, the rate of reaction can be improved by separating the alcohol coproduct that is formed.

In another embodiment, the dispersant is a reaction product of the polyetheramine of formula (I) and an epoxy resin. In one embodiment, the epoxy resin may have an average 1,2-epoxy functionality greater than 1, or at least about 1.4, and still at least about 2.

In one embodiment, the epoxy resin has a 1,2-epoxy equivalency (functionality) on the average of at least 2 to 6.5 epoxide groups per molecule. The epoxy resin can be saturated or unsaturated, linear or branched, aliphatic, cycloaliphatic, aromatic or heterocyclic, and may bear substituents which do not materially interfere during the reaction with the polyetheramine of formula (I). Such substituents can include bromine or fluorine. The epoxy resin may be monomeric or polymeric, liquid or solid, for example, a low melting solid at room temperature. The epoxy resin may be a glycidyl ether prepared by reacting epichlorohydrin with a compound containing at least 1.5 aromatic hydroxyl groups, and carried out under alkaline reaction conditions. In other embodiments, the epoxy resin may be a monoepoxide, a diglycidyl ether of a dihydric compound, an epoxy novolac or a cycloaliphatic epoxy. Generally the epoxy resin contains a distribution of compounds with a varying number of repeat units. Further, the epoxy resin can be a mixture of epoxy resins. For example, in one embodiment, the epoxy resin can comprise a monoepoxide resin and di- and/or a multifunctional epoxy resin having functionalities from 2 to 6.5.

Examples of monoepoxides include, but are not limited to: the glycidyl ethers of phenol, t-butyl phenol, cresol, nonyl phenol, and aliphatic alcohols; and glycidated monoacids and epoxides formed from alpha-olefins and glycidoxyalkylalkoxysilanes.

Other examples of specific epoxy resins which may be used include, but are not limited to, those represented by the formulae:

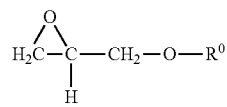

where $R^0$ is a linear or branched alkyl group;

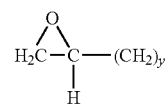

where y is an integer from 1 to 6;

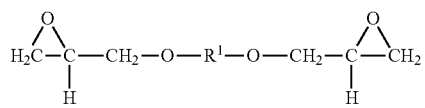

where $R^1$ is an alkyl group, an aryl group, or an arylalkyl group;

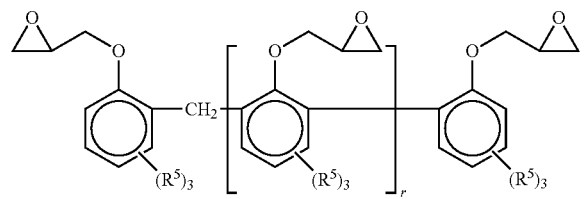

where $R^5$ is independently hydrogen or a $C_1$-$C_{10}$ alkyl group and r is an integer from 0 to 6;

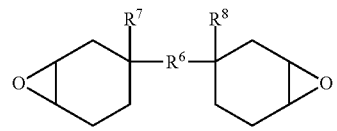

where $R^6$ is a $C_1$-$C_{20}$ alkyl group optionally containing ether or ester group(s) or together with $R^7$ and $R^8$ forms a spiro ring optionally containing heteroatoms, and $R^7$ and $R^8$ are independently hydrogen or together with $R^6$ forms a spiro ring optionally containing heteroatoms. In some embodiments, $R^6$ is a divalent cycloaliphatic group having the formula

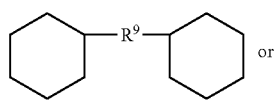 or

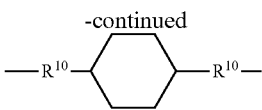

where $R^9$ and $R^{10}$ are each independently a $C_1$-$C_{20}$ alkyl group or an arylalkyl group having the formula

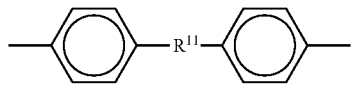

where $R^{11}$ is a $C_1$-$C_{20}$ alkyl group.

According to one embodiment, the epoxy resin is a difunctional epoxy resin selected from a diglycidyl ether of a dihydric phenol, a diglycidyl ether of a hydrogenated dihydric phenol, an aliphatic glycidyl ether, an epoxy novolac and a cycloaliphatic epoxy.

Diglycidyl ethers of dihydric phenols can be produced, for example, by reacting a dihydric phenol and a suitably substituted epichlorohydrin under alkaline conditions, or in the presence of an acidic catalyst with subsequent alkali treatment. Examples of dihydric phenols include, but are not limited to: 2,2-bis(4-hydroxyphenyl) propane (bisphenol-A); 2,2-bis(4-hydroxy-3-tert-butylphenyl) propane; 1,1-bis(4-hydroxyphenyl)ethane; 1,1-bis(4-hydroxyphenyl) isobutane; bis(2-hydroxy-1-naphthyl) methane; 1,5-dihydroxynaphthalene; 1,1-bis(4-hydroxy-3-alkylphenyl) ethane and the like. Suitable dihydric phenols can also be obtained from the reaction of phenol with aldehydes such as formaldehyde (bisphenol-F). Diglycidyl ethers of dihydric phenols also include advancement products of the above diglycidyl ethers of dihydric phenols with dihydric phenols such as bisphenol-A.

Diglycidyl ethers of hydrogenated dihydric phenols can be produced, for example, by hydrogenation of compounds having two free alcoholic hydroxy groups followed by a glycidation reaction with an epihalohydrin in the presence of a Lewis acid catalyst and subsequent formation of the glycidyl ether by reaction with sodium hydroxide. Examples of suitable dihydric phenols include those listed above.

Aliphatic glycidyl ethers can be produced, for example, by reacting an epihalohydrin with an aliphatic diol in the presence of a Lewis acid catalyst followed by conversion of the halohydrin intermediate to the glycidyl ether by reaction with sodium hydroxide. Examples of aliphatic glycidyl ethers include those corresponding to the formulas

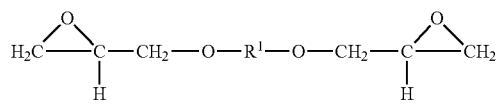

where $R^1$ is $(CH_2)_s$ or

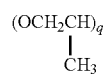

and s is an integer from 2 to 12, and in some embodiments from 2 to 6; and q is an integer from 4 to 24, and in some embodiments from 4 to 12.

Examples of aliphatic glycidyl ethers include, but are not limited to: diglycidyl ethers of 1,4 butanediol; neopentyl glycol; cyclohexanedimethanol; hexanediol; polypropylene glycol and like diols and glycols; and triglycidyl ethers of trimethylol ethane and trimethylol propane.

Epoxy novolacs can be produced by condensation of formaldehyde and a phenol followed by glycidation by reaction of an epihalohydrin in the presence of an alkali. The phenol can be for example, phenol, cresol, nonylphenol and t-butylphenol. Examples of the preferred epoxy novolacs include those corresponding to the formula

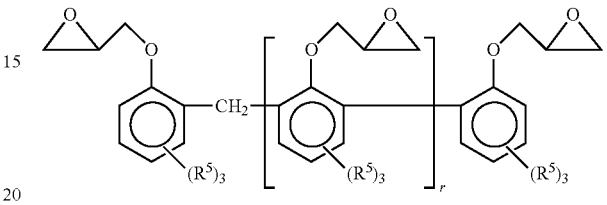

where $R^5$ is independently hydrogen or a $C_1$ to $C_{10}$ alkyl group and r is an integer from 0 to 6. Epoxy novolacs generally contain a distribution of compounds with a varying number of glycidated phenoxymethylene units, r. Generally, the quoted number of units is the number closest to the statistical average, and the peak of the distribution.

Cycloaliphatic epoxies can be produced by epoxidizing a cycloalkene-containing compound with greater than one olefinic bond with peracetic acid. Examples of cycloaliphatic epoxies include those corresponding to the formula

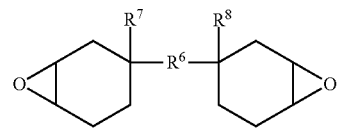

where $R^6$ is a $C_1$ to $C_{20}$ alkyl group optionally containing ether or ester group(s) or together with $R^7$ and $R^8$ form a spiro ring optionally containing heteroatoms, and $R^7$ and $R^8$ are independently hydrogen or together with $R^6$ form a spiro ring optionally containing heteroatoms; or

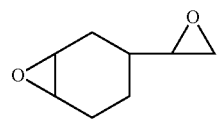

Examples of cycloaliphatic epoxies include, for example, 3,4-epoxycyclo-hexylmethyl-(3,4-epoxy)cyclohexane carboxylate, dicycloaliphatic diether diepoxy [2-(3,4-epoxy)cyclohexyl-5,5-spiro(3,4-epoxy)-cyclohexane-m-dioxane], bis (3,4-epoxy-cyclohexylmethyl)adipate, bis(3,4-epoxycyclohexyl)adipate and vinylcyclohexene dioxide [4-(1,2-epoxyethyl)-1,2-epoxycyclohexane]. Cycloaliphatic epoxies also include compounds of the formulas

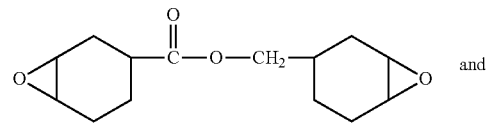

and

-continued

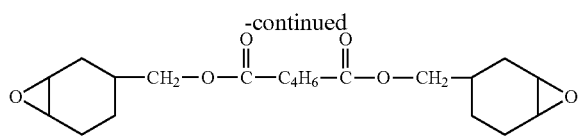

According to another embodiment, the epoxy resin comprises a bisphenol based resin selected from the group of bisphenol A glycidyl ethers, bisphenol F glycidyl ethers, modified bisphenol A glycidyl ethers, modified bisphenol F glycidyl ethers and mixtures thereof.

As discussed above, the dispersant may be a reaction product of the polyetheramine of formula (I) and epoxy resin. It is easy for one of ordinary skill in the art to control the relative amounts of the raw materials used in forming the dispersant. For example, in one embodiment, there is an excess of epoxy resin present, which results in dispersant molecules which are end-capped with epoxy groups. In another embodiment, there is excess polyetheramine used in forming the dispersants, which results in dispersant molecules which are end-capped with amine groups.

In general, the dispersant can be obtained by reacting the epoxy resin with the polyetheramine of formula (I) in excess of epoxides based on equivalents, wherein from about 40% to less than about 90% of the epoxide groups of the starting material are reacted and the epoxy equivalent:amine equivalent ratio is between about 1.10:1 to about 5:1, or between about 1.1:1 to about 4:1, or between about 1.10:1 to about 3:1, or even between about 1.10:1 to about 2.5:1.

In one embodiment, it may be preferred that the polyetheramine of formula (I) and epoxy resin are present in such amounts that the amine group of the polyetheramine is able to be consumed by reacting with essentially all of the epoxide functionality of the epoxy resin. Thus, during the reaction, the amount of polyetheramine of formula (I) is stoichiometrically equal to or greater than the amount of epoxide in the epoxy resin. The resulting product has little, if any, unreacted epoxide functionality left after the reaction.

The reaction may take place at a temperature in the range of 20° C. to 200° C., or in a range of 50° C. to 150° C. In addition, the reaction may be carried out in an inert atmosphere or air. If an inert atmosphere is used, the atmosphere may be nitrogen or argon. Furthermore, the reaction may optionally be carried out in the presence of a solvent. Typically no solvent is necessary, but if present, it may be water or an organic solvent disclosed herein. Finally, reaction times vary independently, and may be any time between about 0.5 hours and about 10 hours.

According to another embodiment, the dispersants described above, which are water soluble, are combined with water to form an aqueous solution. Thus, in some embodiments, the dispersant is soluble in water to a degree of at least 5% by weight of the dispersant, or to a degree of at least 10% by weight of the dispersant, or to a degree of at least 15% by weight of the dispersant, or even to a degree of at least 20% by weight of the dispersant, based on the total weight of the aqueous solution. In still other embodiments, the dispersant is soluble in water to a degree of at least 25% by weight of the dispersant, or to a degree of at least 30% by weight of the dispersant, or to a degree of at least 35% by weight of the dispersant, or even to a degree of at least 40% by weight of dispersant, based on the total weight of the aqueous solution. In still further embodiments, the dispersant is soluble in water to a degree of at least 45% by weight of the dispersant, or to a degree of at least 50% by weight of the dispersant, or to a degree of at least 55% by weight of the dispersant, or even to a degree of at least 60% by weight of dispersant, based on the total weight of the aqueous solution. In one particular embodiment, the dispersant is miscible with water in all proportions.

In another embodiment, the present disclosure provides an aqueous pigment dispersion comprising the dispersant described above, a pigment and a solvent component. The term "aqueous pigment dispersion" herein refers to an aqueous pigment dispersion in which a high concentration of a pigment has been dispersed in water, which serves as a dispersion medium, before production of ink.

The pigment used in the present disclosure is not particularly limited, and organic or inorganic pigments that can be generally used in aqueous pigment dispersions can be employed. Either untreated pigments or treated pigments can be used.

In particular, any known inorganic or organic pigment can be used. Examples of the inorganic pigment include iron oxide and carbon blacks produced by known methods, such as a contact method, a furnace method, and a thermal method. Examples of the organic pigment include azo pigments (including azolake, insoluble azo pigments, condensed azo pigments, and chelate azo pigments), polycyclic pigments (e.g., phthalocyanine pigments, perylene pigments, perinone pigments, anthraquinone pigments, quinacridone pigments, dioxazine pigments, thioindigo pigments, isoindolinone pigments, and quinophthalone pigments), dye chelates (e.g., basic dye chelates and acid dye chelates), nitro pigments, nitroso pigments, and aniline black.

Examples of pigments will now be described by color. Examples of pigments used in black inks include carbon blacks such as No. 2300, No. 2200B, No. 900, No. 960, No. 980, No. 33, No. 40, No. 45, No. 45L, No. 52, HCF88, MA7, MA8, and MA100 manufactured by Mitsubishi Chemical Corporation; Raven 5750, Raven 5250, Raven 5000, Raven 3500, Raven 1255, and Raven 700 manufactured by Columbian Chemicals Company; Regal 400R, Regal 330R, Regal 660R, Mogul L, Mogul 700, Monarch 800, Monarch 880, Monarch 900, Monarch 1000, Monarch 1100, Monarch 1300, and Monarch 1400 manufactured by Cabot Corporation; and Color Black FW1, FW2, FW2V, FW18, FW200, S150, S160, and S170, Printex 35, U, V, and 1400U, Special Black 6, 5, 4, and 4A, NIPEX 150, NIPEX 160, NIPEX 170, and NIPEX 180 manufactured by Degussa AG.

Specific examples of pigments used in yellow inks include C. I. Pigment Yellow 1, 2, 12, 13, 14, 16, 17, 73, 74, 75, 83, 93, 95, 97, 98, 109, 110, 114, 120, 128, 129, 138, 150, 151, 154, 155, 174, 180, and 185.

Specific examples of pigments used in magenta inks include C. I. Pigment Red 5, 7, 12, 48(Ca), 48(Mn), 57(Ca), 57:1, 112, 122, 123, 146, 168, 176, 184, 185, 202, 209, and 269 and C. I. Pigment Violet 19.

Specific examples of pigments used in cyan inks include C. I. Pigment Blue 1, 2, 3, 15, 15:3, 15:4, 16, 22, 60, 63, and 66.

Specific examples of pigments used in white inks include sulfates and carbonates of alkaline earth metals, silicas, such as fine powder of silicic acid and synthesized silicate, calcium silicate, alumina, hydrated alumina, titanium oxide, zinc oxide, talc, and clay. These inorganic white pigments may be subjected to a surface treatment by a variety of surface-treating techniques.

The solvent component used in the present disclosure can be water or a mixture of water and a water-soluble organic solvent. The water used in the present disclosure serves as the dispersion medium of the pigment. Examples of usable water include, but are not limited to, pure water, such as ion exchanged water, ultra-filtrated water, reverse osmotic water, distilled water and ultra-pure water.

These types of water may be used alone or combined with a water-soluble solvent into a mixed solvent component. Examples thereof include a variety of organic solvents, for instance, ketones such as acetone, methyl ethyl ketone, methyl butyl ketone, and methyl isobutyl ketone; alcohols such as methanol, ethanol, 2-propanol, 2-methyl-1-propanol, 1-butanol, and 2-methoxyethanol; ethers such as tetrahydrofuran, 1,4-dioxane, and 1,2-dimethoxyethane; glycols such as dimethyl formamide, N-methyl pyrrolidone, ethylene glycol, diethylene glycol, triethylene glycol, tetraethylene glycol, propylene glycol, polyethylene glycol, and polypropylene glycol; diols such as butane diol, pentane diol, hexane diol, and homologous diols thereto; glycol esters such as propylene glycol laurate; glycol ethers such as ethers of diethylene glycol monoethyl, diethylene glycol monobutyl, and diethylene glycol monohexyl and cellosolve including a propylene glycol ether, a dipropylene glycol ether, and a triethylene glycol ether; alcohols such as methanol, ethanol, isopropyl alcohol, 1-propanol, 2-propanol, 1-butanol, 2-butanol, butyl alcohol, pentyl alcohol, and homologous alcohols thereto; sulfolanes; lactones such as gamma-butyrolactone; lactams such as N-(2-hydroxyethyl) pyrrolidone; and glycerin and derivatives thereof. These water-soluble organic solvents may be used alone or in combination.

The concentration of the dispersant in the aqueous pigment dispersion may be between about 0.1% by weight to about 40% by weight, based on the dry pigment weight. According to another embodiment, the dispersant is present in the aqueous pigment dispersion in an amount of between about 0.5% by weight to about 25% by weight, based on the dry pigment weight. According to yet another embodiment, the dispersant is present the aqueous pigment dispersion in an amount of between about 1% by weight to about 10% by weight, based on the dry pigment weight.

The concentration of the pigment in the aqueous pigment dispersion is normally adjusted to be from about 10% by weight to about 50% by weight, based on the total weight of the aqueous pigment dispersion. In the case where the aqueous pigment dispersion is used to produce ink, the ink can be produced merely by diluting the aqueous pigment dispersion through appropriate addition of water or an additive thereto so that the concentration of the pigment is adjusted to be from about 0.1% by weight to about 30% by weight on the basis of the intended use or physical properties of the ink.

Thus, in some embodiments, the aqueous pigment dispersion of the present disclosure is diluted to adjust the concentration to a predetermined level and can be used in a variety of applications, for example, coating of automobiles and building materials; printing inks such as offset inks, gravure inks, flexographic inks, and silk screen inks; and aqueous ink-jet recording inks.

The amount of solvent component present in the aqueous pigment dispersion according to the present disclosure may be any amount in the range of between about 30% by weight to about 99.8% by weight, and in some embodiments from about 50% by weight to about 95% by weight, or even still from about 70% by weight to about 90% by weight, based on total weight of the aqueous pigment dispersion. Selection of a particular aqueous pigment dispersion as being suitable for a given final-use ink depends on the requirements of the specific application, such as, but not limited to, desired surface tension and viscosity, the selected pigment, drying time of the ink, and type of paper onto which the ink will be printed, as is generally recognized or appreciated by those skilled in the art.

The aqueous pigment dispersion of the present disclosure may optionally include customary auxiliaries from the group consisting of humectants, fillers, flame retardants, preservatives, photoprotectants, surfactants, antioxidants, resins, defoamers and antistats, and preferably in the customary amounts of up to about 20% by weight, based on the total weight of the aqueous pigment dispersion.

In another embodiment, there is provided a method for dispersing a pigment into an aqueous pigment dispersion including admixing the solvent component, a pigment, and about 0.1% by weight to about 40% by weight, based on dry pigment weight, of the dispersant of the present disclosure and subjecting the admixture to shear for a time sufficient to disperse the pigment. The time sufficient to disperse the pigment is typically dependent on the nature of the pigment and dispersant and the equipment which is used and will be determined by the skilled practitioner.

In still another embodiment, the polyetheramine of formula (I) may be used as an additive in a hydrocarbon fuel composition for the prevention and control of piston ring groove deposits, to control intake valve deposit, to clean-up injectors and to remove combustion chamber deposit, and may be particularly suited for use in direct injection spark ignition engines. Typically, the desired deposit control will be achieved by operating an internal combustion engine with a hydrocarbon fuel composition containing a major amount (i.e. at least 50% by weight, based on the total weight of the composition) of a base hydrocarbon fuel comprising hydrocarbons boiling in the gasoline range and a deposit removing effective amount of the polyetheramine of formula (I). The proper concentration of polyetheramine necessary to achieve the desired deposit control will vary depending upon the type of base fuel employed, the type of engine, operating conditions, and the presence of other fuel additives.

In general, the concentration of the polyetheramine of formula (I) employed in the hydrocarbon fuel composition will range from about 500 ppm to about 30,000 parts per million (ppm) by weight, or from about 1,000 ppm to about 20,000 ppm, or from about 2,000 ppm to about 15,000 ppm, or even from about 5,000 ppm to about 10,000 ppm. In one embodiment, the present disclosure is directed to the use of relatively high concentrations of the polyetheramine of formula (I), thus the hydrocarbon fuel composition may comprise greater than about 12,000 ppm of the polyetheramine of formula (I), or from about 12,000 ppm to about 30,000 ppm, or even from about 15,000 ppm to about 25,000 ppm by weight in the hydrocarbon fuel composition.

Other supplemental fuel additives may also be employed with the polyetheramine of formula (I), including, for example, glycol ethers, cyclic carbonates, dispersants, detergents, antioxidants, carrier fluids, metal deactivators, dyes, markers, corrosion inhibitors, biocides, antistatic additives, drag-reducing agents, demulsifiers, dehazers, anti-icing additives, anti-knock additives, anti-valve-seat recession additives, lubricity additives, multifunctional additives (e.g., methylcyclopentadienyl manganese tricarbonyl and/or other cyclopentadienyl manganese tricarbonyl compounds), and combustion improvers. The supplemental fuel additive(s) may be provided in the hydrocarbon fuel composition in an amount necessary to achieve the desired effect.

Suitable base hydrocarbon fuels used in formulating the hydrocarbon fuel compositions according to the present disclosure may include any fuels suitable for use in the operation of spark-ignition internal combustion engines, such as leaded or unleaded motor and aviation gasolines, diesel, and so-called reformulated gasolines which typically contain both hydrocarbons of the gasoline boiling range and fuel-soluble oxygenated blending agents, such as alcohols, ethers and other suitable oxygen-containing organic compounds. Suitable oxygenates include, for example, methanol, ethanol, isopropanol, t-butanol, mixed $C_1$ to $C_5$ alcohols, methyl tertiary butyl ether, tertiary amyl methyl ether, ethyl tertiary butyl ether, and mixed ethers. Oxygenates, when used, will normally be present in the base fuel in an amount below about 25% by volume, for example in an amount that provides an oxygen content in the overall fuel in the range of about 0.5 to about 5% by volume.

The polyetheramine of formula (I) and optional supplemental fuel additive(s) used in formulating the hydrocarbon fuel compositions disclosed herein may be blended into the hydrocarbon base fuel individually or in various sub-combinations. However, it may be desirable in some instances to blend all of the components concurrently using an additive concentrate (i.e., polyetheramine of formula (I), optional supplemental fuel additive(s) and a diluent, such as a hydrocarbon solvent). The use of an additive concentrate takes advantage of the mutual compatibility afforded by the combination of ingredients when in the form of an additive concentrate. Also, use of a concentrate may reduce blending time and may lessen the possibility of blending errors.

The hydrocarbon fuel composition disclosed herein can contact an actuated injector. Non-limiting examples of an actuated injector include direct-injection gasoline, port-fuel, sequential central port-fuel, and direct plate injectors.

Other embodiments of the present disclosure include methods for reducing the formation or persistence of deposits, such as intake valve deposits and chamber combustion deposits, in an engine and eliminating valve sticking in a spark-ignition engine by fueling and/or operating the engine with the hydrocarbon fuel composition disclosed herein.

EXAMPLES

Example 1. Synthesis of 2-Pyrrolidinone Initialized Polyetheramine 2 pounds of 2-pyrrolidinone was mixed with 107 grams of a 45% KOH solution After removing water from the mixture at 120° C., 19.1 pounds of propylene oxide (PO) was added to the reactor. After the alkoxylation reaction was completed, 240 grams of magnesol was used to remove potassium ions. The polyol intermediate was then filtered and reacted with ammonia and hydrogen on a fixed bed reactor in the presence of a metal catalyst. After stripping off the ammonia and water, the polyetheramine product that was obtained was a transparent, clear liquid product having a flashing point of 268° C. and a pH of 12.04. The inventive polyetheramine was found to have a total amine number of about 1.367 meq/g and a total acylatables value of about 1.5479 meq/g. Based on these two numbers, the polyol conversion was calculated to be about 88.3% and the average molecular weight was 646.

Example 2. Synthesis of 2-Pyrrolidinone Initialized Polyetheramine 2 pounds of 2-pyrrolidinone was mixed with 1307 grams of a 45% KOH solution. After removing water from the mixture at 120° C., 23.7 pounds of butylene oxide (BO) was added to the reactor. After the alkoxylation reaction was completed, 292 grams of magnesol was used to remove potassium ion. The polyol intermediate was filtered and reacted with ammonia and hydrogen on a fixed bed reactor in the presence of a metal catalyst. After stripping off the ammonia and water, the polyetheramine product that was obtained was a transparent, clear liquid product having a flashing point of 190° C. and a pH of 11.59. The inventive polyetheramine was found to have a total amine number of about 1.044 meq/g and a total acylatables value of about 1.1233 meq/g. Based on these two numbers, the polyol conversion was found to be about 92.9% and the average molecular weight was 890.

Example 3. Synthesis of ε-Caprolactam Initialized Polyether Amine 2 pounds of ε-caprolactam was mixed with 83 grams of a 45% KOH solution. After removing water from the mixture at 120° C., 14.4 pounds of propylene oxide (PO) was added to the reactor. After the alkoxylation reaction was completed, 185 grams of magnesol was used to remove potassium ion. The polyol intermediate was filtered and reacted with ammonia and hydrogen on a fixed bed reactor in the presence of a metal catalyst. After stripping off the ammonia and water, the polyetheramine product that was obtained was a transparent, clear liquid product having a flashing point of 180° C. and a pH of 11.98. The inventive polyetheramine was found to have a total amine number of about 1.324 meq/g and a total acylatables value of about 1.5742 meq/g. Based on these two numbers, the polyol conversion was found to be about 84.1% and the average molecular weight was 635.

Example 4. Synthesis of ε-Caprolactam Initialized Polyetheramine 2 pounds of ε-caprolactam was mixed with 100 grams of a 45% KOH solution. After removing water from the mixture at 120° C., 17.9 pounds of butylene oxide (BO) was added to the reactor. After the alkoxylation reaction was completed, 225 grams of magnesol was used to remove potassium ion. The polyol intermediate was filtered and reacted with ammonia and hydrogen on a fixed bed reactor in the presence of a metal catalyst. After stripping off the ammonia and water, the polyetheramine product that was obtained was a transparent, clear liquid product having a flashing point of 175° C. and a pH of 11.42. The inventive polyetheramine was found to have a total amine number of about 1.079 meq/g and a total acylatables value of about 1.2992 meq/g. Based on these two numbers, the polyol conversion was found to be about 83% and the average molecular weight was 770.

While the foregoing is directed to embodiments of the present disclosure, other and further embodiments of the disclosure may be devised without departing from the basic scope thereof, and the scope thereof is determined by the claims that follow.

The invention claimed is:
1. A polyetheramine comprising a compound having a formula (I)

wherein R is a cyclic amide group having a formula (II)

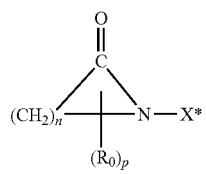
(II)

wherein n is an integer of from 3 to 15, R0 is a substituent that can replace hydrogen in any hydrocarbon portion of the cyclic amide group and is an alkyl group or an aryl group, p is an integer of from 0 to 2n and X* denotes the attachment site of the cyclic amide group to the rest of the cyclic amide initialized polyetheramine compound;

R1 and R2 are each independently hydrogen, methyl or ethyl and each R1 and R2 is independently selected in each —O—CHR1-CHR2- unit;

A is an N-alkyl amino having 1 to about 20 carbon atoms in the alkyl group; and m is an integer ranging from about 2 to about 200.

2. The polyetheramine according to claim 1, wherein R is the cyclic amide group having the formula (II) where n is an integer of from 3 to 12, R0 is an alkyl group and p is an integer of from 0 to 4.

3. The polyetheramine according to claim 2, wherein R is a compound having a formula

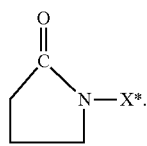

4. The polyetheramine according to claim 2, wherein R is a compound having a formula

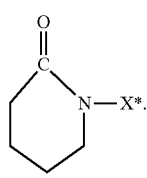

5. The polyetheramine according to claim 2, wherein R is a compound having a formula

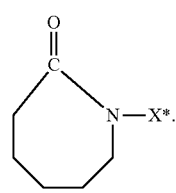

6. The polyetheramine according to claim 1, wherein R1 and R2 are each independently hydrogen, methyl or ethyl and each R1 and R2 is independently selected in each —O—CHR1-CHR2-unit with the proviso that at least one of R1 or R2 is hydrogen; and m is an integer ranging from about 2 to about 40.

7. The polyetheramine according to claim 6, wherein R1 and R2 are each independently hydrogen or methyl.

8. The polyetheramine according to claim 6, wherein R1 and R2 are each independently hydrogen or ethyl.

9. A process for producing the polyetheramine according to claim 1 comprising charging a cyclic amide having a formula

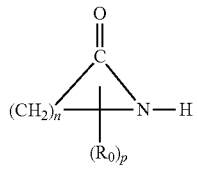

where n is an integer of from 3 to 15, R0 is a substituent that can replace hydrogen in any hydrocarbon portion of the cyclic amide and is an alkyl group or an aryl group and p is an integer of from 0 to 2n to an alkoxylation reaction zone, contacting the cyclic amide with an alkylene oxide in the alkoxylation reaction zone for a period of time to provide an intermediate polyol, charging the intermediate polyol to a reductive amination zone, and contacting the intermediate polyol in the reductive amination zone with a reductive amination catalyst in the presence of a primary alkyl amine.

10. A process for producing the dispersant according to claim 9, comprising reacting from about 0.001 mole to about 2 moles of a polyetheramine comprising a compound having a formula (I)

(I)

wherein R is a cyclic amide group having a formula (II)

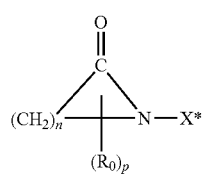
(II)

wherein n is an integer of from 3 to 15, R0 is a substituent that can replace hydrogen in any hydrocarbon portion of the cyclic amide group and is an alkyl group or an aryl group, p is an integer of from 0 to 2n and X* denotes the attachment site of the cyclic amide group to the rest of the cyclic amide initialized polyetheramine compound;

R1 and R2 are each independently hydrogen, methyl or ethyl and each R1 and R2 is independently selected in each —O—CHR1-CHR2- unit;

A is or an N-alkyl amino having 1 to about 20 carbon atoms in the alkyl group; and m is an integer ranging from about 2 to about 200 with 1 mole of the copolymer at a temperature ranging from about 50° C. to about 250° C.

11. A dispersant comprising the reaction product of a polyetheramine according to claim 1, and an epoxy resin.

12. A process for producing the dispersant according to claim 11, comprising reacting a polyetheramine comprising a compound having a formula (I)

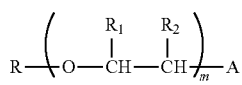
(I)

wherein R is a cyclic amide group having a formula (II)

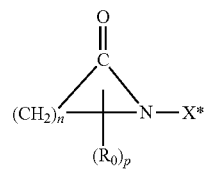
(II)

wherein n is an integer of from 3 to 15, R0 is a substituent that can replace hydrogen in any hydrocarbon portion of the cyclic amide group and is an alkyl group or an aryl group, p is an integer of from 0 to 2n and X* denotes the attachment site of the cyclic amide group to the rest of the cyclic amide initialized polyetheramine compound;

R1 and R2 are each independently hydrogen, methyl or ethyl and each R1 and R2 is independently selected in each —O—CHR1-CHR2- unit;

A is an N-alkyl amino having 1 to about 20 carbon atoms in the alkyl group; and m is an integer ranging from about 2 to about 200 with an epoxy resin at an epoxy equivalent: amine equivalent ratio of between about 1.10:1 to about 5:1 and at a temperature ranging from about 20° C. to about 200° C.

13. An aqueous solution comprising the dispersant according to claim 11, wherein the dispersant is soluble in the aqueous solution to a degree of at least 40% by weight of the dispersant.

14. A hydrocarbon fuel composition comprising a hydrocarbon base fuel and the polyetheramine according to claim 1.

15. The hydrocarbon fuel composition according to claim 14, further comprising a supplemental fuel additive.

16. A method for preventing and/or reducing the formation of deposits in an engine comprising fueling and operating said engine with the hydrocarbon fuel composition according to claim 14.

* * * * *